United States Patent
Hiratsuka et al.

(10) Patent No.: US 7,911,214 B2
(45) Date of Patent: *Mar. 22, 2011

(54) ELECTRICAL RESISTANCE MEASUREMENT METHOD AND COMPONENT INSPECTION PROCESS

(75) Inventors: Yoshiaki Hiratsuka, Kawasaki (JP); Akio Ikeda, Kawasaki (JP); Masaharu Suzuki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 346 days.

This patent is subject to a terminal disclaimer.

(21) Appl. No.: 11/902,323

(22) Filed: Sep. 20, 2007

(65) Prior Publication Data
US 2008/0180115 A1 Jul. 31, 2008

(30) Foreign Application Priority Data
Nov. 30, 2006 (JP) ................................. 2006-322949

(51) Int. Cl.
G01R 27/08 (2006.01)
(52) U.S. Cl. ....................................... 324/691; 324/724
(58) Field of Classification Search ................... 324/691
See application file for complete search history.

(56) References Cited

U.S. PATENT DOCUMENTS
3,818,279 A * 6/1974 Seeger et al. ................. 361/751
4,861,453 A * 8/1989 Matsuoka et al. ............ 204/404
2001/0054904 A1 12/2001 Inoue FOREIGN PATENT DOCUMENTS
| JP | 56-079262 | | 6/1981 |
| JP | 57-154069 | * | 9/1982 |
| TW | 428090 | | 4/2001 |
| TW | 541426 | | 7/2003 |

* cited by examiner

Primary Examiner — Timothy J Dole
Assistant Examiner — Benjamin M Baldridge
(74) Attorney, Agent, or Firm — Fujitsu Patent Center

(57) ABSTRACT

An electrical resistance measurement method and a component inspection process to which the electrical resistance measurement method is applied. In the first step, a measuring object, for example, one pair of zinc-plated steel plates on which surfaces films are formed is prepared. Then, an elastic electroconductive material is sandwiched by the pair of zinc-plated steel plates and a spacer which regulates a space between the zinc-plated steel plates. Next, in the second step, an electrical resistance is measured in a state in which the pair zinc-plated steel plates sandwich the elastic electroconductive material.

8 Claims, 5 Drawing Sheets $R_{1a}$ }
$R_{1b}$ } STEEL PLATE RESISITANCE $R_{1a1}$ }
$R_{1b1}$ } FILM RESISTANCE $R_{10}$: ELECTRO CONDUCTIVE MATERIAL RESISTANCE $Rs = R_{1a} + \underline{R_{1a1}} + R_{10} + \underline{R_{1b1}} + R_{1b}$

ELECTRICAL RESISTANCE MEASUREMENT METHOD AND COMPONENT INSPECTION PROCESS

BACKGROUND OF THE INVENTION

1. Field of the Invention

The present invention relates to an electrical resistance measurement method and a component inspection process. The electrical resistance measurement method is for measuring an electrical resistance of a measuring object on which surface a film is formed. The component inspection process employs the electrical resistance measurement method.

2. Description of the Related Art

Conventionally, as a raw material for a casing of a personal computer and a rack for housing the personal computer, metallic plate materials which provide predetermined strength and simultaneously are easy to supply are widely used.

FIG. 1 is a diagram showing an external appearance of a rack for housing an information processing device such as a personal computer.

A metallic plate material is used in a box 30 and doors 31 of a rack 3 shown in FIG. 1. Thus, when the metallic plate material is used in the box 30 and the doors 31 of the rack 3, the metallic plate material also works as a shielding member to suppress unnecessary radiation from the personal computer to the outside. In the rack 3 shown in FIG. 1, if there is a gap between a door supporting section and the doors, the unnecessary radiation leaks out through the gap to the outside when the personal computer generates the unnecessary radiation. Therefore, an endeavor has been made, for example, an unnecessary-radiation preventing member such as an electroconductive rubber 32 is inserted into the gap in order to obtain a better shielding effect than ever.

In recent personal computers, as their clock rates, which determine their operation speeds, have become high and thereby unnecessary radiations at high frequency tend to increase. Accordingly, metallic plate material (or organic plate materials having electroconductivity may be used when their prices become low enough) are used for the casing, the box 30 and the doors 31 of the rack shown in FIG. 1 in order to enhance the shielding performance.

In order to provide a shielding as described above, it is required to evaluate in advance shielding performance of the metallic plate material itself to be a raw material necessary for manufacturing the casing and the rack.

In evaluating shielding performance of the metallic plate material, an electrical resistance of the metallic plate material is measured using a method compliant to the requirement of JIS-C-2550. Then, the material is evaluated to determine that smaller the measured electrical resistance is, higher the shielding performance the metallic plate material has. However, as the metallic plate material used for providing the casing of the personal computer or the rack, a general-purpose zinc-plated steel plate material and the like which are easy to supply are used. Surface treatment such as an anti-rusting treatment different for each manufacturer may be applied to each of those zinc-plated steel plate materials and the like. Further, even though some are supplied from a same manufacturer, different surface treatment may be applied to them. Therefore, when the above-mentioned evaluation is performed, it is required to measure an electrical resistance including the surface treatment to evaluate characteristics including the surface treatment.

However, when electrical resistance of a metallic plate material is measured with a resistance measurement method compliant to JIS-C-2550, a film formed on a surface of the metallic plate material may be pierced through by a sharp-edged probe used in the method, and thus electrical resistances of the steel plate material excluding the film on the surfaces are measured. As a result, almost same resistances are obtained for different metallic plate materials.

Accordingly, a technique is proposed to solve the above-mentioned problem. In Japanese Patent Application Publication No. S57-154069, a technique to measure an electrical resistance without breaking a film on the surface using an electroconductive rubber is proposed. The electroconductive rubber is used in Japanese Patent Application Publication No. S57-154069 as an electroconductive material whose characteristics are almost the same as a metal, and is used to fill a gap between the box unit and the door as shown in FIG. 1. Or, as described in Japanese Patent Application Publication No. S56-79262, this electroconductive rubber is also used as a member which makes it easy to connect a land pattern on a circuit board with a terminal of a leadless component. When the technique described in Japanese Paten Application Publication No. S57-154069 is used, it is possible to evaluate plate materials each manufactured by different manufacturers as well as those manufactured by a single manufacturer. Accordingly, it is possible to readily select a plate material suitable for manufacturing a casing and a rack.

However, when in the technique of Japanese Patent Application Publication No. S57-154069, each of multiple pieces of the electroconductive rubbers is placed for each measurement point to measure each electrical resistance of the plate material with contacting a probe for each of the multiple pieces of electroconductive rubbers, each condition as to how each electroconductive rubber is compressed may vary the electrical resistance between the electrical rubber and the measuring object because each electroconductive rubber is comparatively large and elastic. Accordingly, with the technique described in Japanese Patent Application Publication 57-154069, it is impossible to accurately measure the electrical resistance of the metallic plate material including the film because the state of the electroconductive rubber is not stable.

SUMMARY OF THE INVENTION

According to the present invention, there is provided an electrical resistance measurement method of measuring an electrical resistance of a plate material on which surface a film is formed, and a component inspection process employing the electrical resistance measurement method.

According to the present invention, a first electrical resistance measurement method of measuring an electrical resistance of a measuring object surface, the electrical resistance measurement method including:

a first step in which an elastic electroconductive material is sandwiched by a pair of the measuring objects; and a second step in which an electrical resistance between the measuring objects in the pair sandwiching the elastic electroconductive material is measured.

According to the first electrical resistance measurement method of the present invention, in the first step, the measuring objects are pressed from their both outer sides to compress the elastic material between the measuring objects so that the both faces of the elastic material closely contact with films on inner faces of the measuring objects. Then, in the second step, an electrical resistance for the each measuring object including an electrical resistance on the films on each surface facing the electroconductive material is measured.

Accordingly, with keeping an elastic electroconductive material (For example, such as an electroconductive rubber, a material in which a sponge is rolled with a sheet of an electroconductive cloth and an electroconductive spring. Hereinafter, referred to an elastic electroconductive material.) to be in a stable state, and with a contact resistance between a probe and the measuring object to be almost zero, it is possible to accurately measure an electrical resistance of the film on the surface of the measuring object.

In other words, when the above-mentioned first electrical resistance measurement method according to the present invention is used for measuring an electrical resistance of a measuring object, an electrical resistance of the measuring object including that of a film formed on a surface thereof is accurately measured.

Here, once it becomes possible to accurately measure an electrical resistance of the measuring object using the first electrical resistance measurement method, it is possible to evaluate manufacturers by comparing results obtained through measuring electrical resistances for the measuring objects each from the manufacturers. In addition, it is also possible to make an evaluation by comparing results obtained through measuring electrical resistances for multiple measuring objects from one manufacturer.

Further, when an electrical resistance between the pair of the measuring objects which are in a state of sandwiching the electroconductive material is measured, a film on surfaces opposite to a surface facing the electroconductive material can be pierced as far as the electrical resistance of the measuring object including those of the films on the surfaces facing the electroconductive material.

Here, it is preferable that the first step is a step in which the electroconductive material and a spacer that regulates a space between the pair of measuring objects are sandwiched by the measuring objects in the pair.

When a pressure is applied between the measuring objects sandwiching the electroconductive materials, thereby compressing the electroconductive material, an electrical resistance value of the electroconductive material may be changed as the pressure changes. Accordingly, when a space between each of the pair of the measuring objects is regulated by the spacer, the compression of the electroconductive material is kept stable. Therefore, the measurement accuracy is enhanced.

Further, it is preferable that the electroconductive material is the elastic electroconductive material such as the electroconductive rubber, a material in which a sponge is rolled with a sheet of an electroconductive cloth and an electroconductive spring, and that the electrical resistance value of the electroconductive material is obtained beforehand.

Such elastic electroconductive materials have been conventionally used, and they each show a stable electrical resistance value to some extent. Accordingly, it is possible to accurately measure an electrical resistance including that of the film formed on a surface of the measuring object by subtracting the electrical resistance value of the elastic electroconductive material from the measurement result.

In addition, it is preferable that the spacer is thinner than a thickness of the electroconductive material in a non-compressed state, and that the spacer is an insulating member.

Accordingly, the insulating spacer which is thinner than the above-mentioned electroconductive material in the non-compressed state regulates a space between the measuring objects in a pair to perform a repeatable measurement in a state in which the elastic electroconductive material is stably compressed to some degree.

In addition, the measuring object may have a film which is formed on a metallic surface and may be made of one of a zinc-plated steel plate, a stainless steel plate, a steel plate, a copper plate, an alloy material, an aluminum and a resin.

Further, according to the present invention, a second electrical resistance measurement method of measuring an electrical resistance of a measuring object surface, the electrical resistance measurement method including:

a first step in which an elastic electroconductive material is sandwiched by a measuring object and a dummy measuring object; and a second step in which an electrical resistance between the measuring object and the dummy measuring object both sandwiching the elastic electroconductive material is measured.

When the electrical resistance measurement is performed using a pair of measuring objects, a total electrical resistance of the pair of measuring objects is obtained. Therefore, one of the measuring objects may be substituted with a dummy measuring object such as a copper plate material to measure an electrical resistance of only one of the measuring objects including the film on the surface using the second electrical measurement method according to the present invention.

In addition, a component inspection process according to the present invention for determining whether a measuring object is excellent or poor based on a measurement result after measuring an electrical resistance of a measuring object surface, the component inspection process including:

a first step in which an elastic electroconductive material is sandwiched by a pair of measuring objects; and a second step in which an electrical resistance between the measuring objects in the pair sandwiching the elastic electroconductive material is measured.

Further, the component inspection process includes each additional feature described above of the electrical resistance measurement method.

When, the electrical resistance measurement method according to the present invention is applied to the component inspection process according to the present invention, the measuring object such as a pair of zinc-plated steel plate materials can be accurately determined as one having an capable shielding performance by measuring an electrical resistance of a surface of the zinc-plated steel plate material.

According to the present invention, an electrical resistance measurement method in which an electrical resistance of a plate material on which a film is formed can be accurately measured is obtained.

DETAILED DESCRIPTION OF THE INVENTION

In the following, an electrical resistance measurement method according to an exemplary embodiment of the present invention will be described with reference to the accompanying drawings.

Figure 1:
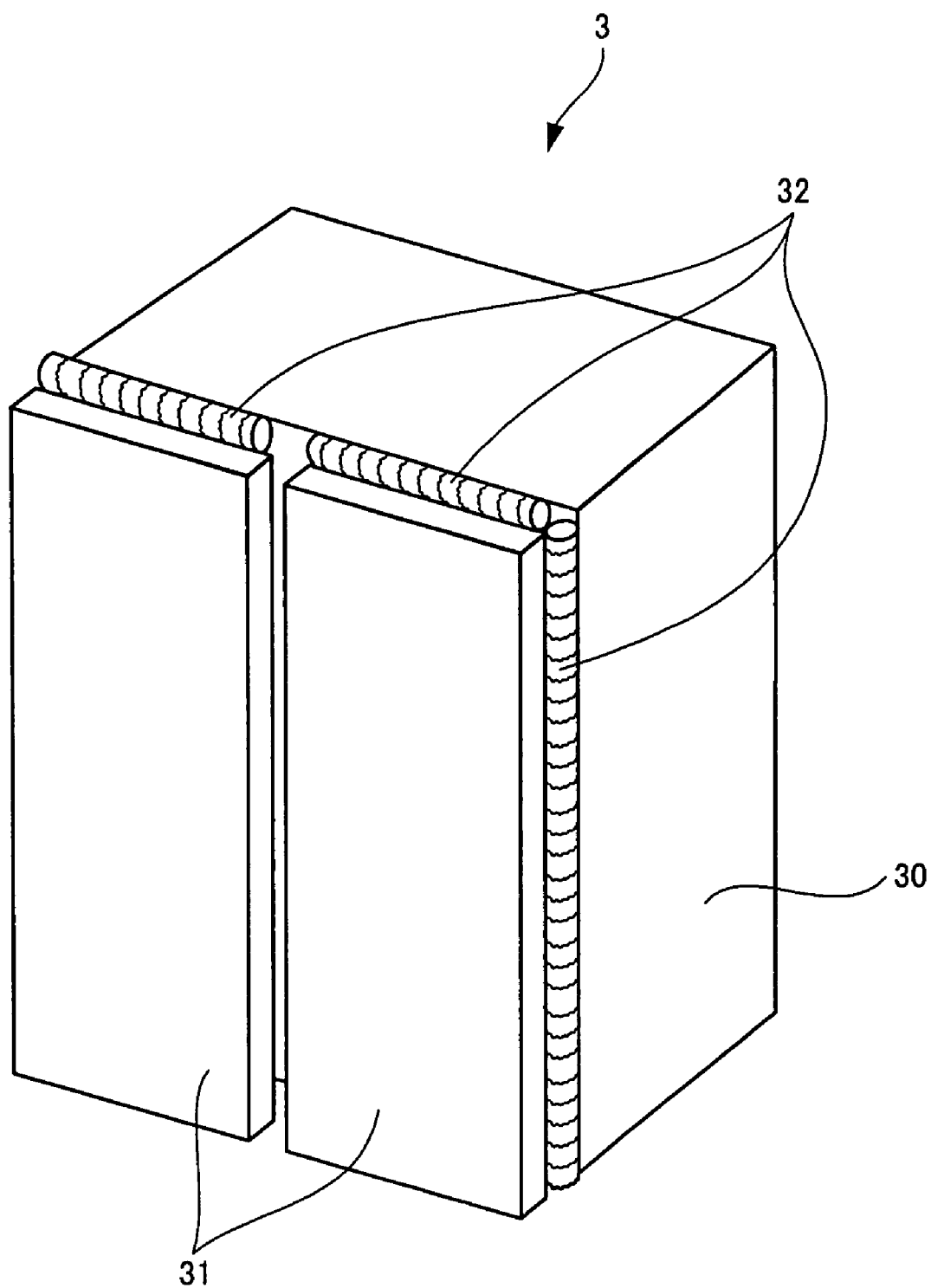
FIG. 1 is a diagram showing an external appearance of a rack for housing a personal computer.
Figure 2:
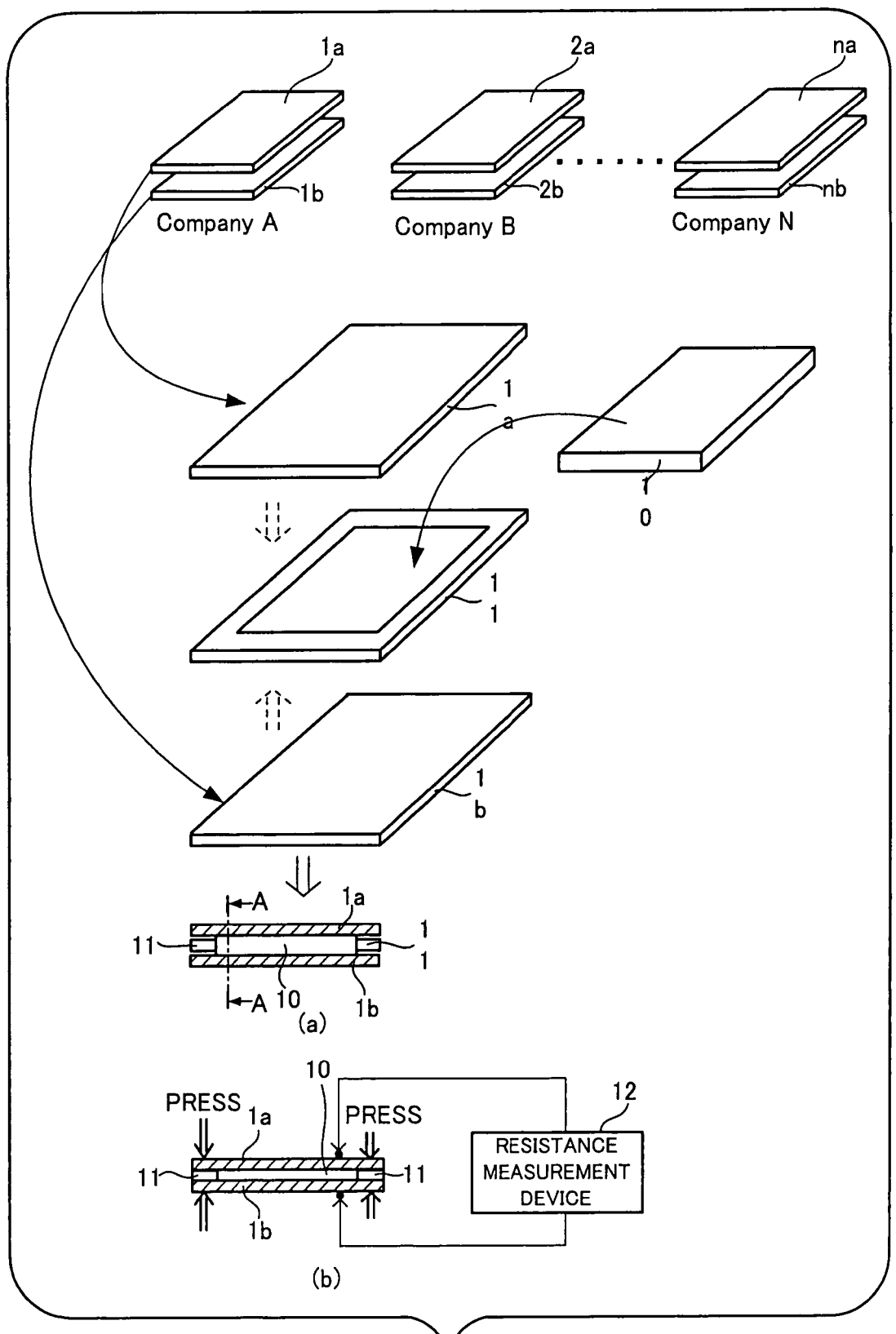
FIG. 2 is an explanatory diagram showing an electrical resistance measurement method for measuring a surface resistance of a metallic plate material to be used as a raw material for a box of a rack and a door shown in FIG. 1.

FIG. 2 is an explanatory diagram showing the electrical resistance measurement method for measuring a surface resistance of a metallic plate material to be used as a raw material for the box of the rack and the door shown in FIG. 1. Part (a) and part (b) of FIG. 2 show a first step and a second step of the electrical resistance measurement method respectively. It is assumed here that the metallic plate material of this example shown in FIG. 2 is supposed to be a zinc-plated steel plate material.

FIG. 2 shows an example in which zinc-plated steel plate materials each manufactured by different manufacturers are measured using the electrical resistance measurement method according to the present invention to evaluate shielding performances of each of the zinc-plated metallic plate materials from the different manufacturers.

First, referring to FIG. 2, elements required for the electrical resistance measurement method according to the present invention will be described.

As the elements required to perform the electrical resistance measurement method according to the present invention, pairs of zinc-plated steel plates 1a and 1b, 2a and 2b to na and nb from a company A, a company B, to a company N are prepared. In addition, elastic electroconductive members 10 each being sandwiched by one of the pairs of zinc-plated steel plates are prepared. Further, spacers 11 which are thinner than the elastic electroconductive members 10 in a non-compressed state are prepared. These spacers 11 are rectangular frames each having an opening for receiving the elastic electroconductive member 10. These spacers 11 are made of an insulating material. After, each of the electroconductive member 10 is arranged to be fit into one of the spacers 11, each of the elastic electroconductive members 10 is sandwiched by one of the pairs of the zinc-plated metallic plates and is compressed until its thickness is equal to that of the spacer 11 to perform the electrical resistance measurement.

Thus, electrical resistances for the pairs of the zinc-plated steel plate materials from the different companies are measured one after another to evaluate shielding performance of the zinc-plated steel plate material from each manufacturer.

Here, the electrical resistance measurement method will be described.

In the first step, as shown in part (a) of FIG. 2, two measuring objects, a pair of the zinc-plated steel plates, for example, two zinc-plated steel plates. 1a and 1b from the company A, sandwich the elastic electroconductive member 10 and the spacer 11 which regulates a space between each of the two zinc-plated steel plates 1a and 1b. The elastic electroconductive member 10 have dimensions which can be fit into a frame of the frame-shaped spacer 11 shown in part (a) of FIG. 2 so that the pair of the zinc-plated steel plates 1a and 1b can sandwich the elastic electroconductive member 10 and the spacer 11.

Then, in the second step as shown in part (b) of FIG. 2, after the pair of the zinc-plated steel plates 1a and 1b are pressed on against each other to compress the elastic electroconductive member 10 until the height thereof is equal to that of the spacer 11, a probe is made to contact to each surface of the pair of the zinc-plated steel plates to measure an electrical resistance.

When a measurement is performed using this electrical resistance measurement method, a distance between each of the pair of the zinc-plated steel plates can be maintained constant by the spacer 11 so that the compressed state of the elastic electroconductive member 10 can be held stably during the measurement. Therefore, an electrical resistance for each of the steel plate materials from those different manufacturers can be measured under the same measurement condition.

Figure 3:
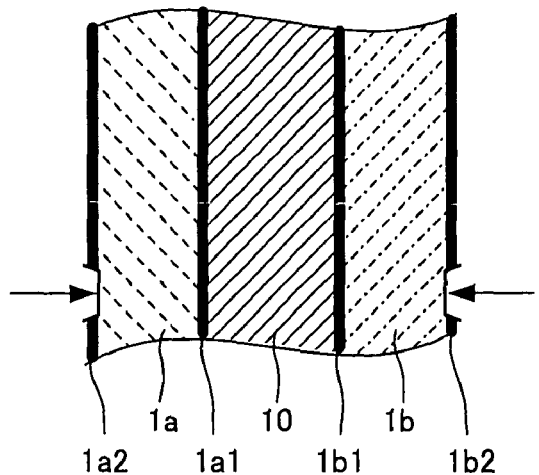
FIG. 3 is a diagram showing a cross section, along the A-A line indicated by the arrows, of a measuring object 1a, an elastic electroconductive material 10 and a measuring object 1b shown in FIG. 2.

FIG. 3 is a diagram showing a cross section, along the A-A line indicated by the arrows, of a measuring object 1a, an elastic electroconductive material 10 and a measuring object 1b shown in FIG. 2.

In the electrical resistance measurement method shown in FIG. 2, in order to enhance the measurement accuracy, it is taken into account that each of those manufacturers applies the same surface treatment to both top and bottom surfaces of each plate material when they apply surface treatment such as a rust prevention film to their plate materials. Accordingly, as shown in FIG. 3, potions of the films 1a2 and 1b2 on the surfaces are scraped off to make area formed by the scraping contact with probes. Then, a measurement of an electrical resistance including those of the films 1a1 and 1b1 formed on the surfaces both facing the elastic electroconductive material 10 is performed. Thus, when the portions of the films 1a2 and 1b2 are thus scraped off for contact with the probes to reduce a contact resistance, it is possible to accurately measure electrical resistances of the zinc-plated steel plates 1a and 1b including electrical resistance of the films formed on the surfaces facing the surfaces of the elastic electroconductive material 10 even if the electrical resistances are considerably low.

Here, referring to FIG. 4, an electrical resistance evaluation method that measures electrical resistance of the material including the films will be described.

Figure 4:
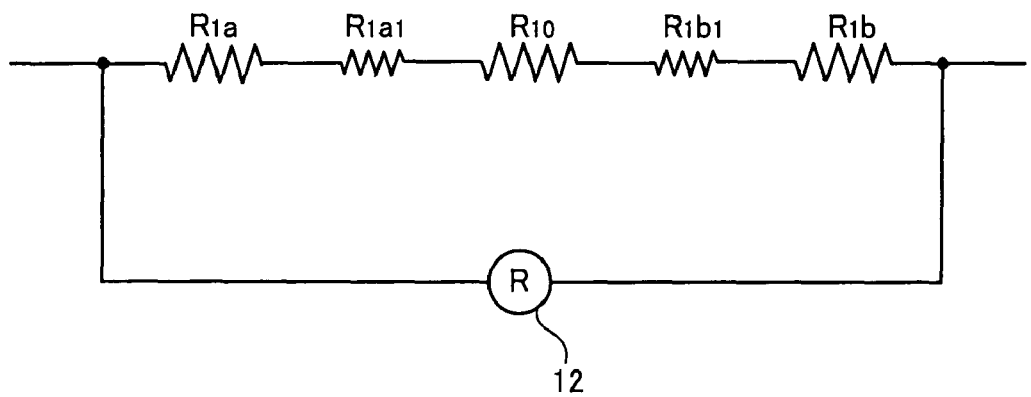
FIG. 4 is an explanatory diagram showing electrical resistance components of the measuring object to be measured by the electrical resistance measurement method shown in FIGS. 2 and 3.

FIG. 4 is an explanatory drawing explaining electrical resistance components of the measuring object to be measured by the electrical resistance measurement method shown in FIGS. 2 and 3. It is assumed here that the electrical resistance R10 of the elastic electroconductive material is measured in advance and is already obtained. In addition, the steel plate material itself of the zinc-plated metallic plate material is assumed to have an electrical resistance almost zero because it is a metal.

As shown in FIG. 3, probes are made to contact with the material while penetrating the respective films on the both surfaces to perform a measurement. Then, a series resistance Rs is measured. The series resistance Rs is calculated by adding a resistance R1a of the zinc-plated steel plate as the measuring object, an electrical resistance value R1a1 of the film of the zinc-plated steel plate is which film is facing the elastic electroconductive material 10, an electrical resistance value R10 of the elastic electroconductive material, an electrical resistance value R1b1 of the film facing the elastic electroconductive material 10, and an electrical resistance value R1b of the zinc-plated steel plate 1b.

After this series electrical resistance value Rs is measured, the R10 of the elastic electroconductive material is subtracted from the measured series electrical resistance value Rs to calculate an electrical resistance value including those of the films of the two zinc-plated steel plates.

After, zinc-plated steel plate materials each from the company A, the company B to the company N are measured to obtain the above-mentioned electrical resistance values, the electrical resistance values of the materials from the respective companies are compared to one another to evaluate shielding performance of each zinc-plated steel plate material. Here, as a result of the electrical resistance values each from the company A to the company N are compared to one another, when a zinc-plated steel plate material has the minimum electrical resistance value, for example from the company B, the zinc-plated steel plate material from the company B is chosen as a raw material for a casing and a rack.

Thus, when the electrical resistances including those of the films are accurately measured in a same condition for each measurement, preferable results are obtained in the comparison to perform careful and fair evaluations.

As described above, the resistance measurement method for accurately measuring electrical resistance of metallic plate materials on which surfaces films are formed is provided.

In addition, in the embodiment described above, as a measuring object, the zinc-plated steel plate material, on which surfaces films are formed is exemplified. However, the measuring object may be an electroconductive organic material on which surfaces films are formed.

However, even if the manufacturer of a zinc-plated steel plate material used in the embodiment has a suitable electric resistance when it is selected as a provider of a material, it may manufacture its zinc-plated steel plate material to provide it as a component, whose electrical resistance is not equal to that suitable resistance obtained at the time of selection.

When a zinc-plated steel plate material, which has a same electrical resistance as that of the selected zinc-plated steel plate material, is used to manufacture racks and casings, those racks and casings precisely have a predetermined shielding performance. However, as the zinc-plated steel plate materials manufactured by the manufacturer may vary in the quality, not all of them have same electrical resistance.

Then, it is preferable to determine a go/no-go decision of acceptance based on the above-mentioned electrical resistance obtained it is selected as a material, when the zinc-plated steel plate materials are inspected as a component.

Figure 5:
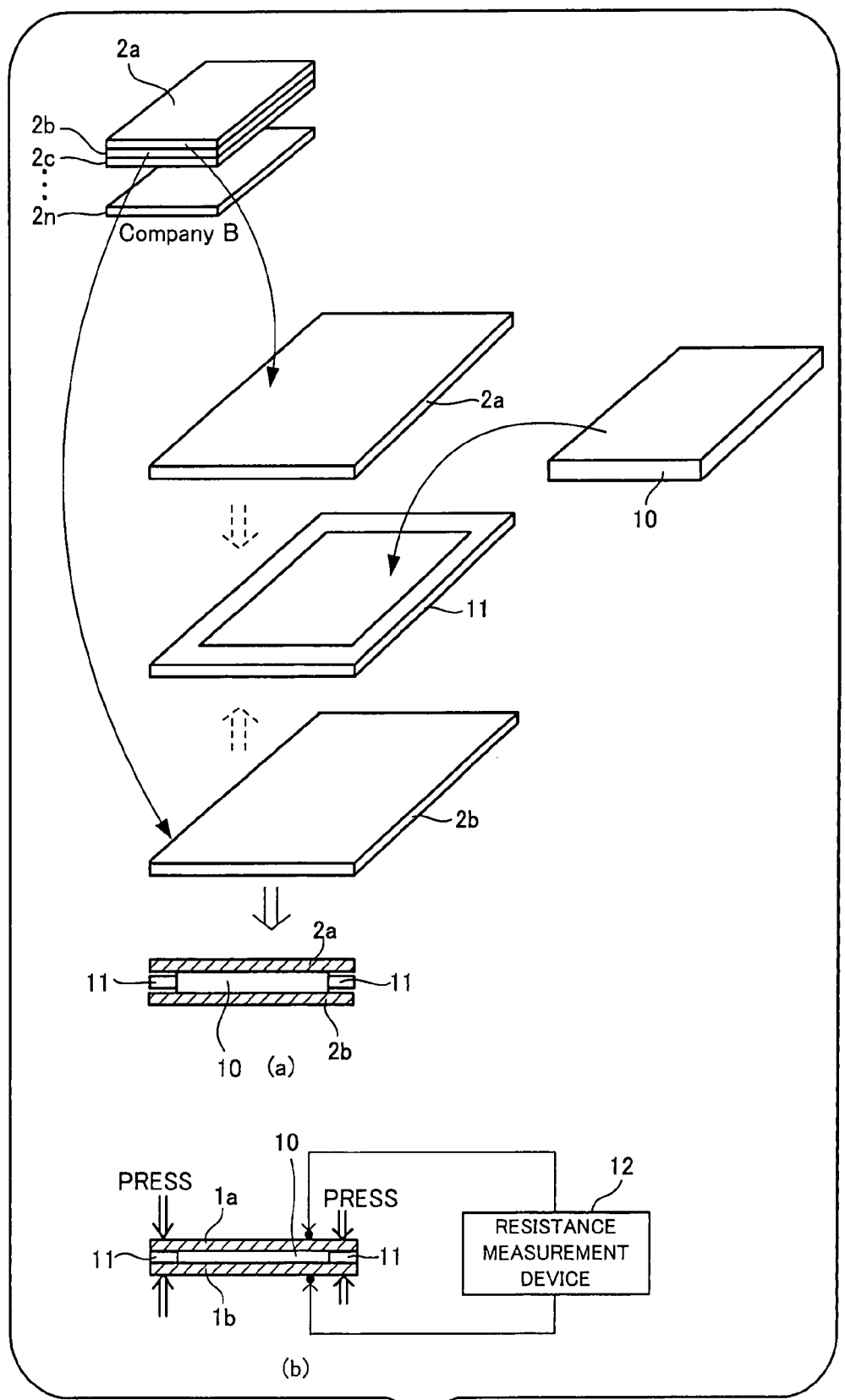
FIG. 5 is a diagram explaining an example in which the electrical resistance measurement method according to the present invention is applied to a component inspection process.

FIG. 5 is a diagram explaining an example in which the electrical resistance measurement method according to the present invention is applied to a component inspection process. FIG. 5 illustrates an example in which the electrical resistance measurement method shown in FIG. 2 is applied to a component inspection process as it is.

Part (a) of FIG. 5 illustrates plural of steel plates 2a to 2n provided from the company B as a selected manufacturer. Two pieces are in sequence picked from the plural of steel plates 2a to 2n to measure electrical resistances using the electrical resistance measurement method shown in FIG. 2 for determining whether or not the measured electrical resistance is less than a predetermined value.

Only when the electrical resistance value measured using the electrical resistance measurement method according to the present invention applied to the component inspection process shown in FIG. 5 is less than a predetermined value, the pair of steel plates as measuring objects pass the acceptance inspection to be accepted and are shipped to a cutting machining site as raw materials for racks and casings.

Thus, when the electrical resistance measurement method according to the present invention is applied to a component inspection process for accepting the component, only zinc-plated steel plates having an electrical resistance with a predetermined shielding performance are accepted to manufacture racks and casings showing the predetermined shielding performance.

In the embodiment described above, steel plates are evaluated in per pair, both two pieces of a pair are determined as defective when the pair fails the inspection. Accordingly, it is preferable that each of the pair failed can be measured separately. In this case, instead of the measuring objects 2a to 2n, a dummy measuring object Dummy can be used to perform measurements.

Figure 6:
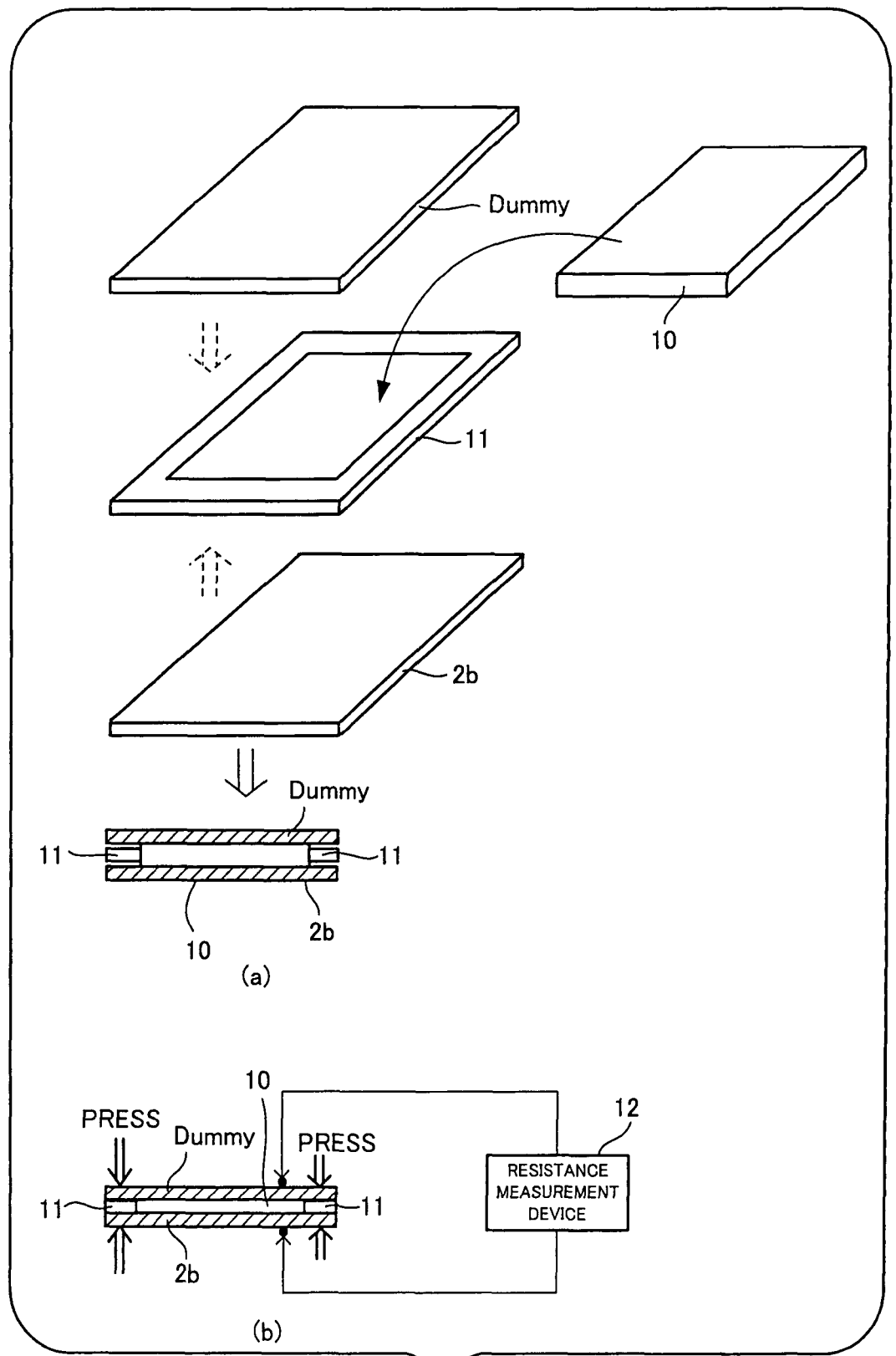
FIG. 6 is a diagram explaining a second embodiment.

FIG. 6 is a diagram explaining an exemplary second embodiment.

As shown in FIG. 6, instead of each pair of the measuring objects 1a to 2n, the dummy measuring object Dummy, for example, a copper plate may be used.

This copper plate is measured in terms of its electrical resistance value in advance similarly to the electroconductive rubber. This copper plate and one piece 2b that is a failed measuring object sandwich the electroconductive rubber 10 to measure an electrical resistance between the measuring object 2b and the dummy measuring object Dummy.

When one of the pair has passed the inspection, it is possible to determine that the passed one is acceptable.

What is claimed is:

1. A method of measuring an electrical resistance of a surface of a measurement object, the method comprising:
    sandwiching an elastic electroconductive material between a pair of measurement objects, wherein the electrical resistance of the elastic electroconductive material is known, the sandwiching includes
        placing the electroconductive material and a spacer between the pair of measurement objects, the spacer is thinner than the electroconductive material in a non-compressed state and regulates a space between the pair of measurement objects;
    measuring an electrical resistance between the pair of measurement objects;
    determining the electrical resistance of the surface of the measurement object based on the measured electrical resistance between the pair of measurement objects and the known resistance of the electroconductive material.

2. The electrical resistance measurement method according to claim 1, wherein the spacer is an insulating member.

3. The electrical resistance measurement method according to claim 1, wherein the measurement object is a metallic plate on whose surface a film is formed.

4. The electrical resistance measurement method according to claim 1, wherein the measurement object is made of one of a zinc-plated steel plate, a stainless steel plate, a steel plate, a copper plate, an alloy material, an aluminum and a resin.

5. A component inspection process for determining the quality of a measurement object based on a measurement result after measuring an electrical resistance of a measurement object surface, the component inspection process comprising:
    sandwiching an elastic electroconductive material between a pair of measurement objects, wherein the electrical resistance of the elastic electroconductive material is known, the sandwiching includes
        placing the electroconductive material and a spacer between the pair of measurement objects, the spacer is thinner than the electroconductive material in a non-compressed state and regulates a space between the pair of measurement objects;
    determining the electrical resistance of the surface of the measurement object based on the measured electrical resistance between the pair of measurement objects and the known resistance of the electroconductive material.

6. The component inspection process according to claim 5, wherein the spacer is an insulating member.

7. The component inspection process according to claim 5, wherein the measurement object is a metallic plate on whose surface a film is formed.

8. The component inspection process according to claim 5, wherein the measurement object is made of one of a zinc-plated steel plate, a stainless steel plate, a steel plate, a copper plate, an alloy material, an aluminum and a resin.

* * * * *